United States Patent
Tonelli et al.

(10) Patent No.: US 7,947,657 B2
(45) Date of Patent: May 24, 2011

(54) METHOD FOR SELECTIVE INHIBITION OF HUMAN N-MYC GENE IN N-MYC EXPRESSING TUMORS THROUGH ANTISENSE AND ANTIGEN PEPTIDO-NUCLEIC ACIDS (PNA)

(75) Inventors: Roberto Tonelli, Granarolo Dell'Emilia (IT); Andrea Pession, Bologna (IT); Raffaele Fronza, Merano (IT); Rosangela Marchelli, Parma (IT); Roberto Corradini, Reggio Emilia (IT); Stefano Sforza, Parma (IT)

(73) Assignees: Universita Degli Studi Di Parma, Parma (IT); Universita Degli Studi Di Bolonga, Bologna (IT)

( * ) Notice: Subject to any disclaimer, the term of this patent is extended or adjusted under 35 U.S.C. 154(b) by 623 days.

(21) Appl. No.: 10/554,291

(22) PCT Filed: Apr. 29, 2004

(86) PCT No.: PCT/IB2004/001297
§ 371 (c)(1),
(2), (4) Date: Sep. 18, 2006

(87) PCT Pub. No.: WO2004/096826
PCT Pub. Date: Nov. 11, 2004

(65) Prior Publication Data
US 2007/0020632 A1    Jan. 25, 2007

(30) Foreign Application Priority Data
Apr. 29, 2003 (IT) .............................. MI2003A0860

(51) Int. Cl.
*C07H 21/02* (2006.01)
*C07H 21/04* (2006.01)
*A61K 31/70* (2006.01)
*C12Q 1/68* (2006.01)

(52) U.S. Cl. .................... 514/44 A; 536/23.1; 536/24.1; 536/24.5

(58) Field of Classification Search .................. None
See application file for complete search history.

(56) References Cited

OTHER PUBLICATIONS

Paula Yurkanis Bruice, "Chimica Organica", Universita degli Studi di Napoli Federico II—Dipartimento di Chimica delle Sostanze Naturali, EdiSES s.r.l.—Napoli, 2005, ISBN 88-7959-301-3, pp. 3-4, 6.

Ugo Azzena et al., "Nuove Prospettive Nella Sintese Degli Acidi Peptido Nucleici", Universita degli Studi di Sassari, Dipartimento di Chimica, SardiniaChem2004, Giornata Di Studio Dedicata Alla Chimica Organica Delle Molecule Biologicamente Attive, May 31, 2004, Aula Magna della Facolta di Scienze—Sassari, pp. 1, 3.

M. Mazzei et al., "Oligonucleotidi Antigene", Gli Ologonucleotidi Sintetici Principi e applicazioni, Consiglio Nazionale delle Ricerche, Progetto Strategico Nucleotidi Antisensa, UTET Periodici Scientifici, 1996, ISBN 88-02-05041-4, pp. 1-2, 77-79.

Sun, Lichun, et al., "Antisense peptide nucleic acids conjugated to somatostatin analogs and targeted at the n-myc oncogene display enhanced cytotoxity to human neuroblastoma IMR32 cells expressing somatostatin receptors", *Peptides* (New York), vol. 23, No. 9, Sep. 2002, pp. 1557-1565.

Doyle, Donald F., et al., "Inhibition of gene expression inside cells by peptide nucleic acids: Effect of mRNA target sequence, mismatched bases, and PNA length", *Biochemistry*, vol. 40, No. 1, Jan. 2000, pp. 53-64.

Galderisi, U., et al., "Antisense inhibitory effect: a comparison between 3'-partial and full phosphorothioate antisense oligonucleotides", *Journal of Cellular Biochemistry*, vol. 74, 1999, pp. 31-37.

Rosolen, A., et al., "Antisense inhibition of single copy N-MYC expression results in decreased cell growth without reduction of C-MYC protein in a neuroepithelioma cell line", *Cancer Research*, vol. 50, No. 19, 1990, pp. 6316-6322.

Cutrona, Gionvanna, et al., "Effects in live cells of a c-myc anti-gene PNA linked to a nuclear localization signal", *Nature Biotechnology*, vol. 18, No. 3, Mar. 2000, pp. 300-303.

Pooga, M., et al., "Cell penetrating PNA constructs regulate galanin receptor levels and modify pain transmission in vivo", *Nature Biotechnology* (New York), vol. 16, 1998, pp. 857-861.

Simmons, C. G, et al., "Synthesis and membrane permeability of pna-peptide conjutgates", *Bioorganic & Medicinal Chemistry Letters* (Oxford), vol. 7, No. 23, Dec. 1997, pp. 3001-3006.

Pession, Andrea, et al., "Targeted inhibition of NMYC by peptide nucleic acid in N-myc amplified human neuroblastoma cells: Cell-cycle inhibitin with induction of neuronal cell differentiation and apoptosis", *International Journal of Oncology*, Feb. 2004, vol. 24, No. 2, pp. 265-272.

*Primary Examiner* — Sean R McGarry
(74) *Attorney, Agent, or Firm* — Pearne & Gordon LLP

(57) ABSTRACT

The present invention refers to sense and antisense peptide nucleic acids (PNAs). The present invention further refers to the use of said PNAs for preparing drugs for treating genetic diseases.

6 Claims, 2 Drawing Sheets

SEQUENCE LISTING

<160> NUMBER OF SEQ ID NOS: 16

<210> SEQ ID NO 1
<211> LENGTH: 16

```
<212> TYPE: DNA
<213> ORGANISM: Artificial Sequence
<220> FEATURE:
<223> OTHER INFORMATION: antisense PNA that is complementary to only
      one sequence in 5'-UT R region of N-myc gene (support at page 6,
      lines 17-20)

<400> SEQUENCE: 1
tccacccagc gcgtcc                                                   16

<210> SEQ ID NO 2
<211> LENGTH: 16
<212> TYPE: DNA
<213> ORGANISM: Artificial Sequence
<220> FEATURE:
<223> OTHER INFORMATION: mutated PNA containing the substitution of
      three bases (support at page 6, lines 23-25)

<400> SEQUENCE: 2
cccactcagc gcgccc                                                   16

<210> SEQ ID NO 3
<211> LENGTH: 16
<212> TYPE: DNA
<213> ORGANISM: Artificial Sequence
<220> FEATURE:
<223> OTHER INFORMATION: sense antigen PNA sequence which is
      complementary to a sequence of exone 2 N-myc gene (support at
      page 8, lines 14-19)

<400> SEQUENCE: 3
atgccgggca tgatct                                                   16

<210> SEQ ID NO 4
<211> LENGTH: 16
<212> TYPE: DNA
<213> ORGANISM: Artificial Sequence
<220> FEATURE:
<223> OTHER INFORMATION: antisense antigen PNA sequence which is
      complementary to a sequence of exone 2 N-myc gene (support at
      page 8, lines 14-19)

<400> SEQUENCE: 4
agatcatgcc cggcat                                                   16

<210> SEQ ID NO 5
<211> LENGTH: 19
<212> TYPE: DNA
<213> ORGANISM: Artificial Sequence
<220> FEATURE:
<223> OTHER INFORMATION: sense primer (exone 2, bp 2366) (support at
      page 14, lines 21-22)

<400> SEQUENCE: 5
cgaccacaag gccctcagt                                                19

<210> SEQ ID NO 6
<211> LENGTH: 21
<212> TYPE: DNA
<213> ORGANISM: Artificial Sequence
<220> FEATURE:
<223> OTHER INFORMATION: antisense primer (exone 2, bp 5095) (support
      at page 14, lines 22-23)

<400> SEQUENCE: 6
tgaccacgtc gatttcttcc t                                             21

<210> SEQ ID NO 7
```

```
<211> LENGTH: 16
<212> TYPE: DNA
<213> ORGANISM: Artificial Sequence
<220> FEATURE:
<223> OTHER INFORMATION: mutated PNA sequence containing the
      substitution of three bases (support at page 15, lines 29-31)

<400> SEQUENCE: 7
gtgccgagca tggtct                                                  16

<210> SEQ ID NO 8
<211> LENGTH: 7
<212> TYPE: PRT
<213> ORGANISM: SV40 virus
<220> FEATURE:
<221> NAME/KEY: misc_feature
<223> OTHER INFORMATION: NLS carrier protein (support at page 7,
      lines 5-6)

<400> SEQUENCE: 8

Pro Lys Lys Lys Arg Lys Val
1               5

<210> SEQ ID NO 9
<211> LENGTH: 16
<212> TYPE: PRT
<213> ORGANISM: antennapedia
<220> FEATURE:
<221> NAME/KEY: misc_feature
<223> OTHER INFORMATION: penetratin carrier protein (support at page 7,
      lines 7-8)

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 24
<212> TYPE: PRT
<213> ORGANISM: Unknown
<220> FEATURE:
<223> OTHER INFORMATION: transportan carrier protein (support at page 7,
      lines 9-10)

<400> SEQUENCE: 10

Gly Trp Thr Leu Asn Ser Ala Gly Tyr Leu Leu Gly Lys Ile Asn Leu
1               5                   10                  15

Ala Ala Leu Ala Lys Lys Ile Leu
            20

<210> SEQ ID NO 11
<211> LENGTH: 16
<212> TYPE: PRT
<213> ORGANISM: Unknown
<220> FEATURE:
<223> OTHER INFORMATION: retro-inverso penetratin carrier protein
      (D)-sequence (support at page 7, lines 11-12)

<400> SEQUENCE: 11

Lys Lys Trp Lys Met Arg Arg Asn Gln Phe Trp Val Lys Val Gln Arg
1               5                   10                  15

<210> SEQ ID NO 12
<211> LENGTH: 13
<212> TYPE: PRT
<213> ORGANISM: HIV virus
<220> FEATURE:
<221> NAME/KEY: misc_feature
<223> OTHER INFORMATION: TAT carrier protein (support at page 7,
```

```
                                -continued
        lines 13-14)

<400> SEQUENCE: 12

Gly Arg Lys Lys Arg Arg Gln Arg Arg Pro Pro Gln
1               5                   10

<210> SEQ ID NO 13
<211> LENGTH: 11
<212> TYPE: PRT
<213> ORGANISM: HIV virus
<220> FEATURE:
<221> NAME/KEY: misc_feature
<223> OTHER INFORMATION: TAT carrier protein (support at page 7,
        lines 15-16)

<400> SEQUENCE: 13

Tyr Gly Arg Lys Lys Arg Arg Gln Arg Arg
1               5                   10

<210> SEQ ID NO 14
<211> LENGTH: 29
<212> TYPE: PRT
<213> ORGANISM: Unknown
<220> FEATURE:
<223> OTHER INFORMATION: carrier peptide sequence (support at page 7,
        lines 17-20)

<400> SEQUENCE: 14

Met Ser Val Leu Thr Pro Leu Leu Leu Arg Gly Leu Thr Gly Ser Ala
1               5                   10                  15

Arg Arg Leu Pro Val Pro Arg Ala Lys Ile His Ser Leu
            20                  25

<210> SEQ ID NO 15
<211> LENGTH: 10
<212> TYPE: PRT
<213> ORGANISM: Unknown
<220> FEATURE:
<223> OTHER INFORMATION: carrier peptide sequence (support at page 7,
        lines 17-19, 21)

<400> SEQUENCE: 15

Lys Phe Phe Lys Phe Phe Lys Phe Phe Lys
1               5                   10

<210> SEQ ID NO 16
<211> LENGTH: 4
<212> TYPE: PRT
<213> ORGANISM: Unknown
<220> FEATURE:
<223> OTHER INFORMATION: carrier peptide sequence (support at page 7,
        lines 17-19, 22)

<400> SEQUENCE: 16

Lys Lys Lys Lys
1
```

METHOD FOR SELECTIVE INHIBITION OF HUMAN N-MYC GENE IN N-MYC EXPRESSING TUMORS THROUGH ANTISENSE AND ANTIGEN PEPTIDO-NUCLEIC ACIDS (PNA)

FIELD OF THE INVENTION

The present invention refers to sense and antisense peptide nucleic acids (PNAs). The present invention further refers to the use of said PNAs for preparing drugs for treating genetic diseases.

PRIOR ART

It is known that antisense strategy can be validly used to treat genetic or virus-related diseases.

According to antisense strategy, a RNA portion complementary to a transcribed RNA region of a gene can block the expression of transcribed RNA by building a bond between complementary DNA and transcribed RNA, so as to prevent the translation of transcribed RNA.

In other words, short DNA sequences comprising 15-25 length bases are synthesized in complementary form and are combined with portions of specific mRNAs of viruses or of noxious origin that are present in tumor cells.

The complementary portions thus built can block translation directly.

Moreover, it is known about the use of antisense strategy for preparing antisense drugs used in human genetic therapy.

It is known about the use of antisense structures such as for instance oligonucleotides.

However, in recent years the use of new antisense and anti-gene structures has developed, such as peptide nucleic acids (PNAs).

Peptide nucleic acids (PNAs) comprise analogs of nucleic acids with neutral charge containing a pseudopeptide chain (backbone) instead of a common deoxyribose-phosphate structure.

Peptide nucleic acids (PNAs) are enzymatically more stable if compared with oligonucleotide antisense structures.

Peptide nucleic acids can bind in a complementary way to DNA/RNA strands, thus creating a hybrid PNA/DNA or PNA/RNA double helix structure, which are thermodynamically more stable than homoduplexes.

Moreover, peptide nucleic acids can be synthesized through synthesis techniques commonly used for the synthesis of peptides.

In the light of the advantages disclosed above, peptide nucleic acids (PNAs) represent an alternative approach for antisense gene therapy and are the most advantageous system for anti-gene strategy.

Furthermore, it has been shown that peptide nucleic acids are highly specific for target sequences and enable to inhibit protein expression.

Therefore, peptide nucleic acids (PNAs) constitute a promising therapeutic approach for treating gene or virus-related diseases.

However, peptide nucleic acids (PNAs) have a drawback, as for oligonucleotide antisense structures, i.e. they have a low capacity of getting through cell membrane.

In order to overcome such drawback, some researchers have tried to conjugate peptide nucleic acids with specific molecules so as to increase the effectiveness of penetration of peptide nucleic acids through cell membrane.

Moreover, it is known that about 25-30% of untreated neuroblastomas show an amplification/overexpression of proto-oncogen N-myc associated with an advanced stage of the disease, rapid progression and unfavorable prognosis.

A neuroblastoma is a sarcoma originated by the peripheral nervous system and consists of neuroblasts (embryonic cells that will turn into nervous cells).

Neuroblastoma strikes children up to 10 years of age and causes cranial and hepatic metastases.

N-myc expression in transgenic mice results in the development of neuroblastomas.

In-vitro antisense inhibition of N-myc expression reduces neuroblastoma proliferation and promotes the differentiation of neuroblastoma tumor cells.

Inhibition has been accompanied until today both by antisense oligonucleotide structures versus mRNA N-myc and by the expression of carriers designed to generate N-myc antisense RNA.

However, oligonucleotide antisenses have a drawback consisting in their rapid degradation due to nucleases.

Therefore, the identification of selective inhibitors of N-MYC (protein) could have a high relevance for the development of specific therapeutic agents with a lower toxicity and a higher effectiveness for treating N-myc expressing neuroblastomas.

As a consequence, there is the need for PNA sequences that can inhibit or eliminate the synthesis of N-MYC protein produced in tumors expressing said protein.

In particular, there is the need for PNA sequences, conjugable if necessary, to be used in antisense and anti-gene strategy so as to inhibit or eliminate the synthesis of N-MYC protein.

In particular, there is the need for antisense PNA sequences and anti-gene PNA sequences to be used for preparing highly specific and effective drugs (antisense and anti-gene drugs) for treating genetic diseases or diseases caused by pathogenic viruses.

In particular, there is the need for selected peptide nucleic acids that can bind messenger mRNA.

AIMS OF THE INVENTION

An aim of the present invention is to design and select PNA sequences that can get through cell membrane.

A further aim of the present invention is to design and select PNA sequences to be used in antisense strategy.

Another aim of the present invention is to design and select PNA sequences to be used in anti-gene strategy.

Another aim of the present invention is to design and select PNA sequences for selective inhibition of N-MYC protein, for instance in human neuroblastoma cells.

Another aim of the present invention is to design and select highly specific and effective PNA sequences for preparing antisense and anti-gene drugs to be used for treating genetic diseases.

These and other aims, as shall be evident from the following detailed description, have been achieved by the Applicant, who proposes an antisense strategy and an anti-gene strategy based on the use of specific peptide nucleic acids (PNAs) for inhibiting the synthesis of N-MYC protein in tumors expressing said protein, in particular in human neuroblastoma cells.

Figure 1:
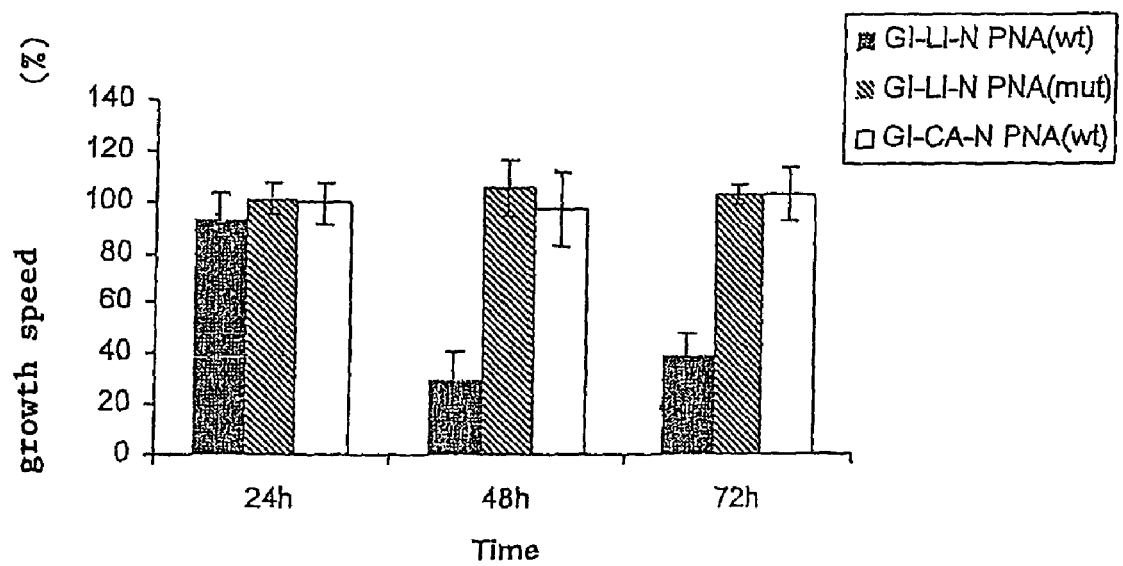
FIG. 1 shows the result of an experiment in which the inhibition effect of antisense PNA for 5'-UTR sequence of N-myc transcript is measured on the growth and proliferation of GI-LI-N and GI-CA-N cells. As control, the inhibition effect is also measured with an antisense PNA for 5'-UTR sequence of N-myc transcript which has three mutation sites introduced into it. The inhibition effects are measured by collecting and counting the cells and measuring their vitality by using colorimetric exclusion method (tryphan blue dye) at 24, 48 and 72 hours.

The inhibitory effect of sense anti-gene PNA is also compared between IMR32 cells and GI-ME-N cells, which shows how the amplification/overexpression of N-myc gene is the factor that allows sense anti-gene PNA to inhibit growth.

DESCRIPTION OF THE INVENTION

Therefore, a first object of the present invention consists in PNA sequences having the characteristics as in the appended independent claim.

Another object of the present invention consist in a process to prepare the PNA sequences having the characteristics as in the appended independent claims.

Another object of the present invention consists in using said PNA sequences for treating genetic diseases, whose characteristics are listed in the appended independent claim.

Other preferred embodiments are listed in the appended dependent claims, although without limiting the object of the present invention.

In a preferred embodiment, the Applicant uses PNA sequences for selective inhibition of N-MYC protein in human neuroblastoma cells.

In order to show the effectiveness of the peptide nucleic acids selected by the Applicant, the latter has carried out experimental tests by selecting four neuroblastoma cell lines: GI-LI-N, IMR-32 where N-myc gene is amplified and overexpressed; and GI-CA-N, GI-ME-N where N-myc gene is not amplified and is not expressed.

Surprisingly, the Applicant has found out that the antisense peptide nucleic acids selected by the Applicant can get through cell membrane without using a carrier.

Furthermore, the Applicant has surprisingly found out that the inhibition effect, due to antisense and anti-gene PNAs, on the synthesis of N-MYC protein is highly selective and specific and has an anti-proliferating effect.

Moreover, the stop of the growth of human neuroblastoma GI-LI-N cells with amplified N-myc gene, after the use of antisense PNAs, is directly followed by cell differentiation or apoptosis (programmed cell death).

Advantageously, peptide nucleic acid (PNA) comprises 12 to 24 nucleotide bases. Said peptide nucleic acid is complementary to the sense or antisense strand of human N-myc gene.

Preferred PNAs as described below and disclosed by way of example below, are not however to be regarded as limiting the present invention. As a matter of fact, other types of PNA can also be carried out, by suitably modifying their structure, so as to improve their effectiveness and make them more specific and suitable to various therapeutic needs. Also these possible variants therefore fall within the framework and aims of the present invention.

In a first embodiment, peptide nucleic acid is complementary to the sense strand of human N-myc gene and is referred to as antisense PNA.

In a second embodiment, peptide nucleic acid is complementary to the antisense strand of human N-myc gene and is referred to as sense PNA.

The Applicant has designed an antisense peptide nucleic acid PNA (bp 135-150: SEQ ID NO: 1, genbank accession number M13241) that is complementary to only one sequence in 5'-UTR region of N-myc gene so as to inhibit an attack with the ribosome.

In order to assess how specific the activity of antisense PNA is, a mutated PNA containing the substitution of three bases has been designed (SEQ ID NO: 2).

Antisense or sense PNA can be conjugated with a carrier that can get through the nuclear membrane of target cells, i.e. of tumor cells expressing N-myc gene.

Preferably, said carrier is conjugated in 3' to end of PNA sequence.

In a preferred feature of the invention, said carrier consists of suitable peptide sequences deriving from appropriate proteins.

Said proteins are of various origin; for instance, they can derive from different types of viruses.

By way of absolutely non-limiting example, said proteins can be preferably selected among:
  Nuclear localization signal (NLS), from SV40 virus: the carrier consists of a peptide sequence SEQ ID NO: 8;
  Penetratin, from antennapedia; the carrier consists of a peptide sequence SEQ ID NO: 9;
  Transportan: the carrier consists of a peptide sequence SEQ ID NO: 10;
  Retro-inverso penetratin: the carrier consists of a peptide sequence SEQ ID NO: 11;
  TAT protein, from HIV virus: the carrier consists of a peptide sequence SEQ ID NO: 12;
  TAT protein, from HIV virus: the carrier consists of a peptide sequence SEQ ID NO: 13.

Other peptide sequences to be used preferably as carriers can be selected for instance among the following ones:
  SEQ ID NO: 14;
  SEQ ID NO: 15
  SEQ ID NO: 16.

The amino acids constituting said peptide sequences can be both in L and in DL configuration.

In another preferred feature of the invention, PNA is conjugated with carriers selected among peptides comprising amino acids with D or L configuration, whereby said peptides are bound directly to PNA through a stable covalent bond or through a disulfur labile bond, which can then be opened by reduction.

Peptides comprising D-arginine are particularly preferred.

In a third preferred feature of the invention, PNA is conjugated with carriers having various structures, whereby said carriers are bound directly to PNA through a stable covalent bond or through a disulfur labile bond, which can then be opened by reduction.

Among these carriers, retinoic acid is particularly preferred.

Antisense PNA conjugated with a carriers shows an antigene PNA activity. Among anti-gene PNAs, those which bind to the antisense strand of N-myc gene are referred to as sense anti-gene PNAs, whereas those which bind to the sense strand of N-myc gene are referred to as antisense anti-gene PNAs.

Sense anti-gene PNAs have proved particularly effective towards target cells.

The Applicant has also designed sense anti-gene PNA and antisense anti-gene PNA sequences (sense anti-gene: bp: 1650-1655 SEQ ID NO: 3; antisense anti-gene SEQ ID NO: 4 genbank accession number M13241), which are complementary to a sequence of exon 2 N-myc gene. Said sequences have been conjugated in 3' with a nuclear localization signal (NLS) deriving from SV40 virus, so as to help it to get through nuclear membrane. The carrier consists of a peptide sequence SEQ ID NO: 8.

In a preferred embodiment, antisense PNAs and sense antigene or antisense anti-gene PNAs according to the present invention are used for preparing pharmaceutical compositions.

In the following, by mere way of example, a method for the synthesis of peptide nucleic acids (PNAs) according to the present invention on micromolar scale 10, purification and characterization is described:

50 mg of polystyrene resin functionalized with methylbenzhydrylamino groups (MBHA-PS) are treated with dichloromethane (DCM) for 1 hour so as to make the resin swell. The resin is then washed with 5% diisopropylethylamine (DIPEA) in dimethylformamide (DMF), DCM, further 5% DIPEA in DMF and N-methylpyrrolidone (NMP). A solution containing 0.01 millimoles of the first N-Boc protected C-terminal PNA monomer (available on the market) in 125 microliters of NMP, 0.0095 millimoles of hexafluorophosphate benzotriazolyluronium (HBTU) in 125 microliters of NMP, is prepared separately, and the two solutions are mixed together. 0.02 millimoles of DIPEA are added and the whole is let activate for 2 minutes, then the solution containing the activated monomer is put into contact with the resin. The reaction goes on for 1 hour, then the resin is washed repeatedly with NMP. Unreacted sites are blocked with a solution of acetic anhydride/pyridine/DMF in a ratio of 1:2:2 put into contact with the resin for 1 hour. The absence of reactive sites is checked through a Kaiser test. In case of non-negative Kaiser test, blocking procedure is repeated. The resin is then washed repeatedly with NMP, then with 5% DIPEA in DMF, then with DMC. The resin is now bound to the first C-terminal monomer in a ratio of 0.2 millimoles/gram.

The procedure of chain lengthening consists, for every monomer to be inserted, in a cycle including: Boc group de-protection, pre-activation and coupling, block of unreacted sites if present (capping). Such cycles are usually carried out by means of an automatic synthesizer (Applied Biosystem ABI 433A). The solutions used for the various steps are listed below. De-protection: trifluoroacetic acid (TFA)/m-cresol 95:5; pre-activation and coupling: 0.05 millimoles of protected N-Boc PNA monomer and 0.048 millimoles of HBTU dissolved in 500 microliters of NMP and added with 0.1 millimoles of DIPEA; capping: acetic anhydride:pyridine:NMP 1:25:25. Rhodaminated PNAs have been synthesized using a spacing molecule (Boc-amino-ethoxyethoxyacetic acid) in the last-but-one cycle instead of PNA monomer, and rhodamine in the last cycle instead of PNA monomer.

PNAs thus synthesized have been separated from the resin by means of solution of trifluoromethanesulfonic acid (TFMSA):TFA:m-cresol:thioanisol 2:6:1:1 and precipitated with the addition of ethyl ether to the separation solution.

Raw PNAs thus obtained have been analyzed through LC-MS (analytical column C18 250×4.6 mm, gradient elution between water added with 0.2% formic acid and a solution of water:acetonitril 60:40 added with 0.2% formic acid, flow rate 1 ml/min. UV detector at 260 nm and mass detector in positive ionization mode, range 150-1500 m/z). Purification has been carried out using a system resembling the analytical one, though using a semi-preparative column (250×10 mm). The identity of the pure compound has always been confirmed by mass spectrometry. Typical yield after purification: 30%. Typical purity after purification: 90-95%.

In order to assess the ability of antisense PNAs and of anti-gene PNAs to get into human neuroblastoma cells and to analyze the subsequent intracellular localization, the Applicant has used four cell lines GI-LI-N and IMR-32, GI-CA-N and GI-ME-N- and has treated them for 30 minutes to 24 hours with 20 μM of antisense or sense PNA conjugated with rhodamine in 5'. Anti-gene PNAs were further conjugated with NLS in 3'.

The picture on the fluorescent microscope shows that intracytoplasmatic fluorescence for 5'-UTR antisense PNA (in cell lines GI-LI-N and GI-CA-N) and intranuclear fluorescence for anti-gene PNAs (in cell lines GI-LI-N and GI-ME-N) can already be measured 30 minutes after cell treatment with PNA. Maximum intensity is achieved in 6 hours, then the level is constant for 24 hours.

High intracytoplasmatic values of antisense PNA were observed, whereas for anti-gene PNAs high intranuclear values were observed.

Untreated cells only show a background intracellular fluorescence after six hours.

In order to assess the effectiveness and specificity of the peptide nucleic acids selected by the Applicant, the latter has used the four cell lines described above.

In threefold tests using plates with 24 wells, $1.0 \times 10^5$ cells have been introduced into the first wells with 0.5 ml of RPMI1640 containing 10% of FBS and 2 mM of L-butanine.

Cells have been incubated for 24 hours so as to let them adhere to the base of the wells.

Then, in order to assess the optimal concentration for cell growth inhibition, peptide nucleic acid has been added to GI-LI-N cells in concentration of 10, 20, 40 and 60 μM for 5'-UTR antisense PNA, whereas for sense and antisense anti-gene PNAs in concentrations of 1, 2, 5, 10 and 20 μM on GI-LI-N and IMR-32 cells- In order to assess the specificity and selectivity of the effect of peptide nucleic acids onto N-MYC protein, GI-LI-N cells have been treated with a variant of 5'-UTR antisense peptide nucleic acid with three mutation sites incorporated therein, in a concentration of 20 μM (optimal concentration selected for such PNA), and GI-CA-N cells (which do not have any amplification of N-myc gene) have been treated with 5'-UTR antisense PNA in a concentration of 20 μM.

In order to assess the specificity of sense and antisense anti-gene PNAs, GI-ME-N and GI-CA-N (in which N-myc gene is not amplified and is not expressed) have been treated with sense and antisense anti-gene PNA in a concentration of 10-1M (optimal concentration selected for sense anti-gene PNA).

Then, in order to assess the effects of the treatments, cells have been collected and counted 24, 48 and 72 hours after treatment.

Cells counting and vitality has been determined using colorimetric exclusion method (tryphan blue dye).

The treatment with 20 μM antisense PNA in GI-LI-N cells with amplified N-myc gene expression, shows a high inhibition of cell growth. The maximum inhibition effect is of 70% and is achieved 48 hours after treatment (FIG. 1).

Conversely, GI-CA-N neuroblastoma cells with non-amplified N-myc gene expression and not expressing N-myc, do not show any inhibition effect in the tests carried out under the same conditions (FIG. 1).

Proliferation tests on GI-LI-N cells using an antisense PNA containing a sequences altered by the introduction of three mutation sites, have not shown any inhibition effect (FIG. 1). This proves the selective and specific action of antisense PNA for 5'-UTR sequence of N-myc transcript.

The production of N-MYC (protein) was assessed using Western Blotting in GI-LI-N cell line after treatment with 20 μM antisense PNA in 24, 48 and 72 hours. An evident reduction of the protein level after 24 hours has been found. Said reduction decreases after 72 hours.

A flow cytometric analysis on GI-LI-N cells 36 hours after treatment with 20 μM of antisense PNA, shows that said PNA induces a cell accumulation in $G_0/G_1$ from 34% to 57% and decreases in $G_2$ and in S phase from 13 to 6% and from 53% to 37%, respectively.

Moreover, the number of cells in sub-$G_1$ phase with a hypodiploic DNA content (lower number of chromosomes than diploid DNA, i.e. 2n) increases from 3 to 22%.

In order to assess the differentiation of GI-LI-N cells towards neuronal cells, said cell line has been treated with 20 μM antisense PNA, whereby morphologic changes have been detected by means of microscopic analysis.

Microscope assessment has been carried 36 and 48 hours after GI-LI-N cell growth in the presence or absence of 20 μM antisense PNA.

After 36 hours treated cells have a less uniform distribution than control cells, and after 48 hours they tend to form small cell aggregates.

No effect of growth inhibition has been found for GI-CA-N cells, but said effects have been found in tests made on GI-LI-N cells.

Advantageously, the PNAs according to the present invention show a high degree of selectivity for the target designed on 5'-UTR N-myc sequence.

As further confirmation, no inhibition effect has been observed in cell vitality, in cell cycle and in the amount of N-MYC protein also after treatment with 10 μM mutated antisense PNA. This further shows the specificity of the effect of antisense PNA.

Anti-gene PNA: the treatment with 10 μM sense anti-gene PNA in GI-LI-N and IMR-32 cells with amplified N-myc gene expression, causes a high inhibition of cell growth.

Figure 2:
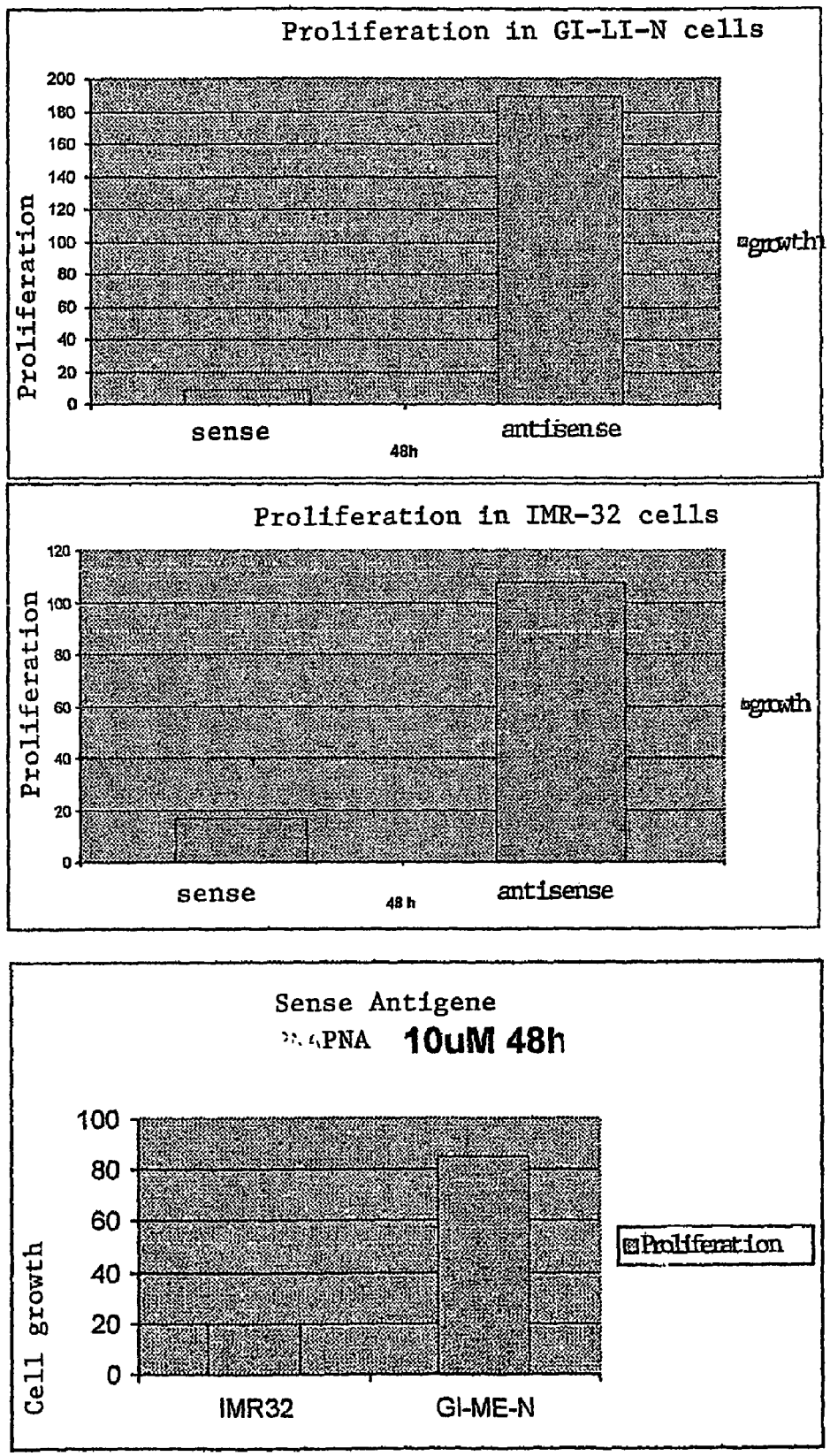
FIG. 2 shows the inhibition effect of treatment with 10 μM sense anti-gene PNA in the proliferation of GI-LI-N and IMR-32 cells with amplified N-myc gene expression after 48 hours; while conversely 10 μM antisense anti-gene PNA do not show any inhibition effect.

As a matter of fact, the maximum inhibition effect is of 90% in GI-LI-N cells and of 80% in IMR-32 cells and is achieved 48 hours after treatment (FIG. 2; C(a) and D(b)).

Conversely, neuroblastoma GI-ME-N and GI-CA-N cells with non-amplified and non-expressed N-myc gene, do not show any inhibition effect in the tests made under the same conditions (FIG. 2; E(c)).

Proliferation tests on GI-LI-N and IMR-32 cells using 10 μM antisense anti-gene PNA have not shown any inhibition effect (FIG. 2; C(x) and D(y)). This proves that the action of sense anti-gene PNA is selective and specific for the antisense strand of N-myc gene, and that the action of transcription inhibition is likely to unfold itself through the stop of RNA polymerase, which uses as template its own antisense strand.

The production of N-myc transcript was assessed before and after hours treatment with 10 μM sense anti-gene PNA by amplification in PCR of cDNA obtained from 250 ng of mRNA of GI-LI-N cells. The following primers have been used: sense SEQ ID NO: 5 (ExonE 2, by 2366); antisense SEQ ID NO: 6(Exon 3, by 5095) (Genbank M13241). PCR has been carried out with 30 reaction cycles. The results have shown that in GI-LI-N cells treated with sense anti-gene PNA, the PCR product of N-myc transcript cannot be detected, whereas it can easily be detected in untreated cells.

Advantageously, anti-gene PNAs according to the present invention are highly specific for N-myc amplification/overexpression.

The presence of an amplification/overexpression of N-myc gene is the main characteristic distinguishing GI-LI-N, IMR-32 cell lines from GI-ME-N and GI-CA-N cell lines.

No effect of growth inhibition has been found for GI-ME-N and GI-CA-N cells, but said effects have been found in tests made on IMR-32 cells.

Advantageously, the anti-gene PNAs according to the present invention show a high degree of selectivity for the target designed on exon 2 sequence of N-myc.

As a matter of fact, anti-gene PNA has a high inhibitory effect, since it interferes directly with PNA polymerase during the transcription in the antisense strand, whereas the complementary antisense anti-gene PNA has a much lower effect, likely due only to the steric interference with the transcription protein complex.

In further tests on sense anti-gene PNA, the production of N-MYC protein was assessed by using Western Blotting in IMR-32 cell line after 3 hours of treatment with 10 μM sense anti-gene PNA. A reduction of 50% of protein level has been detected after 3 hours of treatment with sense anti-gene PNA.

A cytofluorimetric analysis in IMR-32 cells 24 and 48 hours after the treatment with sense anti-gene PNA in a concentration of 10 μM, induced a cell accumulation in $G_0/G_1$ (from 39% to 53% after 24 hours; from 31% to 53% after 48 hours) and decrease in $G_2/M$ (from 17% to 6% after 24 hours; from 25% to 9% after 48 hours) and S phase (from 45 to 41% after 24 hours; from 44% to 39% after 48 hours).

In order to assess how specific the activity of sense anti-gene PNA is, a mutated PNA containing the substitution of three bases has been designed (SEQ ID NO: 7).

No inhibition effect has been observed in cell vitality, in cell cycle and in the amount of N-MYC protein also after treatment with a concentration of 10 μM of mutated anti-gene PNA and under the same test conditions used for sense anti-gene PNA. This proves the specificity of the effect of sense anti-gene PNA.

The treatment with 10 μM sense anti-gene PNA has also been carried out in HT29 cells (deriving from colon carcinoma) and in HeLa cells (deriving from cervical carcinoma) expressing N-myc gene.

The treatment causes a high inhibition of cell growth. As a matter of fact, the maximum inhibition effect is of 70% in HT29 cells 48 hours after treatment, and of 70% in HeLa cells 24 hours after treatment.

Proliferation tests on HT29 and HeLa cells using 10 μM mutated sense anti-gene PNA have not shown any inhibition effect. This proves that also in colon and cervical carcinomas expressing N-myc, there is an inhibition effect using sense anti-gene PNA, and that such action is selective and specific for the antisense strand of N-myc gene.

The PNAs according to the present invention are interesting for the development of PNA-based drugs for specific treatments and neuroblastomas expressing N-MYC protein.

Such PNAs can also be used for other types of tumors expressing

N-MYC protein such as for instance retinoblastoma, medulloblastoma, neuroblastoma, glioblastoma, astrocytoma or lung small cell tumor, rhabdomyosarcoma, B-type acute lymphoblastic leukemias.

The invention claimed is:

1. Peptide nucleic acid (PNA) complementary to the antisense or sense strand of human N-myc gene, wherein said peptide nucleic acid is SEQ ID NO: 3 being complementary to the exon 2 sequence of N-myc gene, or said peptide nucleic acid is SEQ ID NO: 1 being an only sequence complementary to 5'-UTR region of human N-myc gene.

2. The peptide nucleic acid (PNA) according to claim 1, in which PNA is conjugated with a carrier that can get through the nuclear membrane of target cells expressing N-myc gene.

3. The conjugated peptide nucleic acid (PNA) according to claim 2, in which said carrier is conjugated at 3' end of PNA sequence.

4. The peptide nucleic acid (PNA) according to claim 2, in which said carrier is chosen among the following peptide sequences:
SEQ ID NO: 8;
SEQ ID NO: 9;
SEQ ID NO: 10;
SEQ ID NO: 11;

SEQ ID NO: 12;
SEQ ID NO: 13;
SEQ ID NO: 14;
SEQ ID NO: 15;
SEQ ID NO: 16.

5. The peptide nucleic acid (PNA) according to claim 1, in which sense anti-gene PNA is conjugated in 3' with SEQ ID NO: 8.

6. A pharmaceutical composition comprising a peptide nucleic acid PNA according to claim 1.

* * * * *